United States Patent

Baumgarth et al.

[11] 4,264,585
[45] Apr. 28, 1981

[54] HYDROCORTISONE ESTERS, PHARMACEUTICAL FORMULATIONS CONTAINING THESE AND PROCESSES FOR THEIR PREPARATION

[75] Inventors: Manfred Baumgarth; Dieter Orth; Jürgen Harting, all of Darmstadt, Fed. Rep. of Germany

[73] Assignee: Merck Patent Gesellschaft mit Beschränkter Haftung, Darmstadt, Fed. Rep. of Germany

[21] Appl. No.: 92,318

[22] Filed: Nov. 8, 1979

[30] Foreign Application Priority Data

Nov. 8, 1978 [DE] Fed. Rep. of Germany ....... 2848423

[51] Int. Cl.³ .............................................. A61K 31/56
[52] U.S. Cl. ................................ 424/243; 260/397.45
[58] Field of Search ................... 260/397.45; 424/243

[56] References Cited

U.S. PATENT DOCUMENTS 2,736,733  2/1956  Rogers et al. .................. 260/397.45
4,119,626  10/1978  Schulze et al. .................... 260/397.4

Primary Examiner—Elbert L. Roberts
Attorney, Agent, or Firm—Millen & White

[57] ABSTRACT

Hydrocortisone esters of the formula

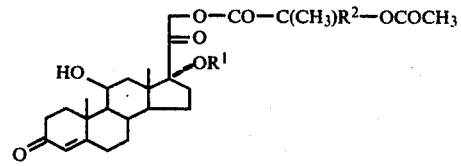

wherein $R^1$ is H, formyl or acetyl and $R^2$ is H or $CH_3$ are antiphlogistically active.

10 Claims, No Drawings

HYDROCORTISONE ESTERS, PHARMACEUTICAL FORMULATIONS CONTAINING THESE AND PROCESSES FOR THEIR PREPARATION

SUMMARY OF THE INVENTION

The present invention relates to new hydrocortisone esters. An object of this invention is to provide new compounds having valuable properties, especially those which can be used for the preparation of medicaments.

Upon further study of the specification and appended claims, further objects and advantages of this invention will become apparent to those skilled in the art.

These objects have been attained by providing new hydrocortisone esters of Formula I

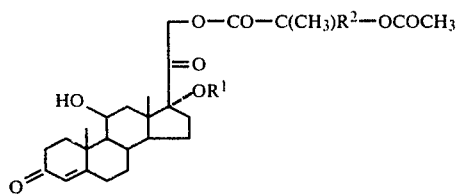

wherein $R^1$ is H, formyl or acetyl and $R^2$ is H or $CH_3$.

DETAILED DISCUSSION

In Formula I, $R^1$ is preferably H or acetyl. $R^2$ is preferably H. Accordingly, the invention relates in particular to those compounds of Formula I in which at least one of $R^1$ and $R^2$ has one of these preferred meanings.

The present invention also relates to a process for the preparation of the compounds of Formula I, comprising reacting a steroid of Formula II

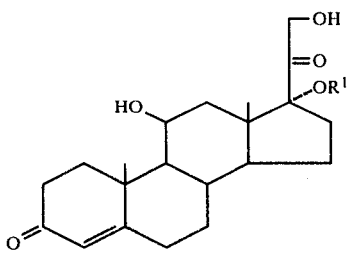

wherein $R^1$ is as defined above, or a functionally modified derivative thereof, with a 2-hydroxy-fatty acid of Formula III

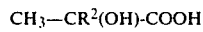

$$CH_3-CR^2(OH)\text{-}COOH \qquad III$$

wherein $R^2$ is as defined above, or with a functionally modified derivative thereof, and, for those resultant compounds having an OH in the substituent in the 21-position, acetylizing this OH group.

In other respects, the hydrocortisone esters of Formula I are prepared by methods which are in themselves known, such as those described in the literature (for example in the standard works such as Houben-Weyl, Methoden der organischen Chemie (Methods of Organic Chemistry), Georg-Thieme-Verlag, Stuttgart and Organic Reactions, John Wiley and Sons, Inc., New York) and, specifically, under reaction conditions which are known and suitable for these reactions. Use can also be made of variants which are in themselves known and are not mentioned in more detail herein.

Functionally modified derivatives of the steroids of Formula II include preferably the corresponding 21-iodide compounds or the 21-methane-sulfonates and also the 21-p-toluenesulfonates. Functionally modified derivatives of the compounds of Formula III include preferably the corresponding carboxylic acid halides, especially the chlorides and bromides, and the corresponding acid anhydrides, and also the corresponding derivatives containing an acetylated hydroxyl group on $C_{(2)}$.

The compounds III can be racemic or optically active. Accordingly, the compounds of Formula I include those forms which are racemic and optically active in respect of the asymmetric C atoms in the substituent in the 21-position.

The steroids of Formula II are preferably reacted with acids of the formula $CH_3-CR^2(OCOCH_3)-COOH$ (IIIA) or the derivatives thereof which are functionally modified at the carboxyl group, such as, for example, the halides (for example chlorides) or anhydrides thereof, appropriately at temperatures of $-100°$ to $+200°$ C. and preferably about $-20°$ to $+150°$ C. The reaction times vary from about 1 minute to 48 hours and preferably 10 minutes to 24 hours.

When one of the above mentioned acids IIIA is employed as the esterifying agent, the reaction can be carried out without or with the addition of catalysts, such as sulfuric acid, hydrogen chloride, phosphoric acid, aromatic sulfonic acids, such as p-toluenesulfonic acid, or acid ion exchangers, and, in particular, preferably at temperatures of 10° to 150° C. The acid IIIA is usually employed in excess.

The reaction can also be carried out in the presence of water-binding agents, for example molecular sieves or anhydrous heavy metal sulfates, such as copper sulfate, iron sulfate, nickel sulfate, cobalt sulfate or zinc sulfate. The water formed during the esterification can also be removed by azeotropic distillation, and hydrocarbons, such as benzene or toluene, or chlorinated hydrocarbons, such as chloroform or 1,2-trichloroethane, are advantageously added as inert organic solvents.

Under very mild conditions, the esterification proceeds if the water of reaction is bonded chemically by the addition of carbodiimides, such as N,N'-dicyclohexylcarbodiimide, preferably in molecular amounts, the reaction being carried out in inert solvents such as ether, dioxane, benzene or ethylene glycol dimethyl ether, or preferably in bases such as pyridine.

The steroids of Formula II can also be reacted with functionally modified derivatives of the acids IIIA, for example with their halides or anhydrides, without or with the addition of acid-binding agents, for example of sodium hydroxide or potassium hydroxide, sodium carbonate or potassium carbonate, or of an organic base such as pyridine, quinoline, collidine or triethylamine. Suitable solvents include inert organic solvents, such as ether, tetrahydrofuran or benzene. It is also possible to use excess halides or anhydrides or an excess of the base as the solvent. The esterification reaction is approximately carried out at temperatures of $-20°$ to 150° C. and preferably 0° to 30° C. and as a rule takes 10 minutes to 24 hours.

It is also possible to use functionally modified derivatives of the steroids II as the starting materials and, in particular, to use the corresponding 21-iodosteroids. These are producible by reacting the steroids II with methanesulfonyl chloride to give the corresponding 21-methanesulfonyloxy-steroids and subsequently replacing the methanesulfonyloxy group by iodine. The 21-iodosteroids are preferably reacted with the carboxylic acids III or IIIA in the presence of amines such as triethylamine or pyridine, or also with the salts of these carboxylic acids, for example, the alkali metal, alkaline earth metal, magnesium, zinc or ammonium salts, preferably the sodium or potassium salts. The reaction is as a rule carried out in the presence of an inert solvent, such as acetone or ether. The reaction temperatures are about 40° to 120° C. and preferably 40° to 70° C.; the reaction times are about 1 to 15 hours and, in general, 5 to 10 hours.

If the resulting product still contains a free hydroxyl group in the substituent in the 21-position, this group is subsequently acetylated by a conventional mild acetylation method. This can be effected, for example, by reaction with an excess of acetic anhydride in pyridine at room temperature. During the acetylation, the less reactive hydroxyl group in the 11-position of the hydrocortisone is not attacked.

It has been found that the compounds of Formula I possess valuable pharmacological properties coupled with good tolerance. In particular, antiphlogistic effects are displayed which can be ascribed, for example, to an antiproliferative active component (detectable, for example, analogously to the method of Rudas, Drug Research 10, 226 (1969)), an antiexsudative active component (detectable, for example, analogously to the method described by Hotovy and Kapff, Arch. Int. Pharmacodyn., 111, 420–436 (1957); granuloma pouch test), a thymolytic active component (detectable, for example, analogously to the method of Steelman et al, Steroids 1, 163 (1963)), and an active component which influences the ACTH (detectable on the basis of the inhibition of an adrenal hypertrophy analogously to the method of Bohus, B., Acta Physiol. Acad. Sci. Hung. 29, 203 (1966)). The compounds of Formula I are therefore suitable, for example, for combating persistent allergies and other inflammatory diseases of the skin and also for the treatment of rheumatic arthritis. These actions are detectable by the test methods conventional for this purpose.

The compounds of Formula I can therefore be used as medicinally active compounds for treating patients in human medicine and, e.g., mammals, in veterinary medicine and can also be used as intermediates for the preparation of other medicinally active compounds.

The present invention, thus, also relates to the use of the new compounds of Formula I for the preparation of pharmaceutical formulations, especially by a non-chemical route. The compounds I can be brought into a suitable dosage form together with at least one solid, liquid and/or semi-liquid excipient or auxiliary and, optionally, in combination with one or more additional active compounds.

The present invention also relates to agents, especially pharmaceutical formulations, containing at least one compound of Formula I.

These formulations can be used as medicaments in human medicine and in veterinary medicine. Excipients which are suitable include organic or inorganic substances which are particularly suitable for topical application and do not react with the new compounds, for example water, vegetable oils, hydrocarbons such as alkylated naphthalenes, halogenated hydrocarbons such as $CF_2Cl_2$ (for example, for aerosols), benzyl alcohols, polyethylene glycols, glycerol triacetate, gelatin, carbohydrates, such as lactose or starch, magnesium stearate, talc and petroleum jelly. The formulations used for topical application include in particular solutions, lotions, emulsions, sprays (aerosols), ointments, creams, pastes or powders. The new compounds can also be lyophilized. The indicated formulations can be sterilized and/or contain auxiliaries such as lubricants, preservatives, stabilizers and/or wetting agents, emulsifiers, salts for influencing the osmotic pressure, buffer substances, dyes and/or aroma generating substances. They can, if desired, also contain one or more additional active compounds, for example, one or more antibiotics, such as gentamycin and/or antimycotics and/or other substances having a topical action.

The new compounds are as a rule administered analogously to known anti-inflammatory agents available commercially (for example hydrocortisone 17-butyrate). For topical application in combination with excipients suitable for this purpose, a good activity can be determined over relatively wide dilution ranges.

For example, concentrations of the active compound of about 0.05 to 1 percent by weight, based on the weight of the preparation used, are effective for healing inflammations. Concentrations of about 0.1 to 0.5 percent by weight are preferred.

For oral or parenteral administration, the daily dosage is generally about 0.01 to 1 mg/kg of body weight. Unit dosages are about 0.5 to 50 mg, preferably 5 to 25 mg.

Each of the compounds of the Formula I named in the examples which follow is particularly suitable for the preparation of pharmaceutical formulations.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

11.16 g of acetyllactic acid chloride is added dropwise, with the exclusion of moisture, at 0° to 5°, to a solution of 10 g of hydrocortisone 17-acetate in 100 ml of pyridine; the mixture is stirred for one hour at 20° and then poured into 5% ice-cold hydrochloric acid; and the precipitate is extracted with methylene chloride. The extract is washed with water, saturated sodium bicarbonate solution and water and dried over sodium sulfate. Evaporation and chromatography of the residue on silica gel (solvent system: methylene chloride/petroleum ether/acetone 10:10:3) gives hydrocortisone 17-acetate 21-(2-acetoxypropionate) of m.p. 115°–117° (from ether); $[\alpha]_D^{20} = +64.2°$ ($CHCl_3$).

EXAMPLES 2 to 6

The following compounds are obtained analogously to EXAMPLE 1 from hydrocortisone, hydrocortisone 17-formate or hydrocortisone 17-acetate with acetyllactic acid chloride or 2-acetoxy-isobutyric acid chloride:
2. Hydrocortisone 17-acetate 21-(2-acetoxyisobutyrate), m.p. 114°–117° (from acetone).
3. Hydrocortisone 21-(2-acetoxypropionate), m.p. 182°–183° (from acetone); $[\alpha]_D^{20} = +185.1°$ ($CHCl_3$).

4. Hydrocortisone 21-(2-acetoxyisobutyrate), m.p. 180°-181° (from acetone/ether/petroleum ether).
5. Hydrocortisone 17-formate 21-(2-acetoxypropionate).
6. Hydrocortisone 17-formate 21-(2-acetoxyisobutyrate).

EXAMPLE 7

170 g of acetyllactic anhydride [b.p. 107° under 0.01 mm Hg; can be prepared by reacting lactic acid with acetyl chloride and subsequently treating the resulting acetyllactic acid (b.p. 110° under 5 mm Hg) with dicyclohexylcarbodiimide in ether] is added, with the exclusion of moisture, to 188.8 g of hydrocortisone 17-acetate in 144 ml of pyridine and the mixture is left to stand for 2 hours at 20°. The mixture is poured into ice-water and extracted with methylene chloride. The extract is washed with water, 10% hydrochloric acid, saturated sodium bicarbonate solution and water and dried over sodium sulfate. Evaporation yields hydrocortisone 17-acetate 21-(2-acetoxypropionate), m.p. 115°-117° C. (from ether); $[\alpha]_D^{20} = +64.2°$ (CHCl$_3$).

EXAMPLE 8

8 g of acetyllactic acid and then 4 g of dicyclohexylcarbodiimide are added to 4 g of hydrocortisone 17-acetate in 80 ml of pyridine; the mixture is stirred for 20 hours with the exclusion of moisture; and the product which has precipitated is filtered off. Water is added to the filtrate and the mixture is acidified with dilute hydrochloric acid and then extracted with ethyl acetate. The organic phase is washed with sodium bicarbonate solution and water, dried over sodium sulfate and evaporated, and hydrocortisone 17-acetate 21-(2-acetoxypropionate) is obtained; m.p. 115°-117° (from ether); $[\alpha]_D^{20} = +64.2°$ (CHCl$_3$).

EXAMPLE 9

A solution of 23.5 g of 21-dehydroxy-21-iodohydrocortisone (obtained by the action of methanesulfonyl chloride on hydrocortisone and subsequent reaction of the resulting hydrocortisone 21-methanesulfonate with sodium iodide in acetone), 6.6 g of acetyllactic acid and 8.8 ml of triethylamine in 1,000 ml of acetone is boiled for 7 hours and then evaporated to about half its volume. The solution is poured into water and neutralized and the resulting hydrocortisone 21-(2-acetoxypropionate) is filtered off; m.p. 115°-117° (from ether); $[\alpha]_D^{20} = +64.2°$ (CHCl$_3$).

EXAMPLE 10

A solution of 23.5 g of 21-dehydroxy-21-iodohydrocortisone, 4.5 g of lactic acid and 8.8 ml of triethylamine in 1,000 ml of acetone is reacted, and worked up, analogously to Example 9. The crude hydrocortisone 21-(2-hydroxypropionate) is then left to stand with 200 ml of dry pyridine and 100 ml of acetic anhydride for 3 hours at 25°. The mixture is then stirred into ice-water, the precipitate is isolated and hydrocortisone 21-(2-acetoxypropionate) is obtained; m.p. 115°-117° (from ether); $[\alpha]_D^{20} = +64.2°$ (CHCl$_3$).

The examples which follow relate to pharmaceutical formulations which contain compounds of the Formula I (percentages are percentages by weight).

EXAMPLE A: OINTMENT

| | | |
|---|---|---|
| Hydrocortisone 17-acetate 21-(2-acetoxy-propionate) | | 0.25% |
| Anhydrous wool fat | | 2.0% |
| Viscous paraffin | | 10.0% |
| White petroleum jelly | to make up to | 100.0 |

EXAMPLE B: CREAM

| | |
|---|---|
| Hydrocortisone 17-acetate 21-(2-acetoxy-propionate) | 0.5% |
| Cetyl alcohol | 9.0% |
| Viscous paraffin | 3.0% |
| Glycerol monostearate | 2.0% |
| Propylene glycol monostearate | 2.0% |
| Glycerol | 2.0% |
| Very finely divided silica | 0.1% |
| Petroleum jelly | 10.0% |
| Polyoxyethylenesorbitane monopalmitate | 30.0% |
| Methyl p-hydroxybenzoate | 0.065% |
| Propyl p-hydroxybenzoate | 0.035% |
| Propylene glycol | 3.0% |
| Water    to make up | 100.0% |

EXAMPLE C: LOTION

| | |
|---|---|
| Hydrocortisone 17-acetate 21-(2-acetoxy-propionate) | 0.2% |
| Viscous paraffin oil | 10.0% |
| Ethanol | 2.0% |
| Glycerol | 1.0% |
| Propylene glycol | 2.0% |
| Sorbic acid | 0.15% |
| Fatty alcohol polyglycol ether | 2.0% |
| Mixture of cetylstearyl alcohol and sodium cetylstearylsulfate and a non-ionic emulsifier | 0.5% |
| Perfume oil of lily-of-the-valley | 0.01% |
| Water    to make up to | 100.0% |

EXAMPLE D: OINTMENT

| | | |
|---|---|---|
| Hydrocortisone 17-acetate 21-(2-acetoxy-propionate) | | 0.1% |
| Gentamycin sulfate (based on free gentamycin base) | | 0.1% |
| Cetyl alcohol | | 2.4% |
| Anhydrous wool fat | | 1.0% |
| Viscous paraffin | | 15.0% |
| White petroleum jelly | to make up to | 100.0 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A hydrocortisone ester of the formula

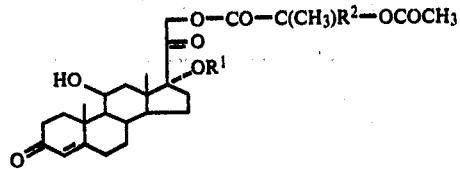

wherein R¹ is H, formyl or acetyl and R² is H or CH₃.

2. A hydrocortisone ester of claim 1, wherein R¹ is H or acetyl.

3. A hydrocortisone ester of claim 1, wherein R² is H.

4. Hydrocortisone 21-(2-acetoxypropionate), a compound of claim 1.

5. Hydrocortisone 17-acetate 21-(2-acetoxypropionate), a compound of claim 1.

6. Hydrocortisone 21-(2-acetoxyisobutyrate), a compound of claim 1.

7. Hydrocortisone 17-acetate 21-(2-acetoxyisobutyrate), a compound of claim 1.

8. A pharmaceutical composition which comprises an antiphlogistically effective amount of a compound of claim 1 and a pharmaceutically acceptable carrier.

9. A method of treating inflammation in a patient which comprises administering to the patient an antiphlogistically effective amount of a compound of claim 1.

10. The method of claim 9, wherein the administration is topical.